(12) United States Patent
Thyrann et al.

(10) Patent No.: US 8,946,482 B2
(45) Date of Patent: Feb. 3, 2015

(54) SALTS OF RASAGILINE AND PHARMACEUTICAL PREPARATIONS THEREOF

(75) Inventors: Thomas Thyrann, Allschwill (CH); Christian Janssen, Illerkirchberg (DE); Ramesh Matioram Gidwani, Maharasthra (IN)

(73) Assignee: Ratiopharm GmbH, Ulm (DE)

( * ) Notice: Subject to any disclaimer, the term of this patent is extended or adjusted under 35 U.S.C. 154(b) by 0 days.

(21) Appl. No.: 13/383,163

(22) PCT Filed: Jul. 7, 2010

(86) PCT No.: PCT/EP2010/059723
§ 371 (c)(1),
(2), (4) Date: Feb. 24, 2012

(87) PCT Pub. No.: WO2011/003938
PCT Pub. Date: Jan. 13, 2011

(65) Prior Publication Data
US 2012/0142966 A1    Jun. 7, 2012

(30) Foreign Application Priority Data
Jul. 9, 2009 (IN) .......................... 1632/CHE/2009

(51) Int. Cl.
| | | |
|---|---|---|
| C07C 211/00 | (2006.01) |
| A01N 33/02 | (2006.01) |
| C07C 211/42 | (2006.01) |
| C07C 53/122 | (2006.01) |
| C07C 53/126 | (2006.01) |
| C07C 57/12 | (2006.01) |

(52) U.S. Cl.
CPC ............. *C07C 211/42* (2013.01); *C07C 53/122* (2013.01); *C07C 53/126* (2013.01); *C07C 57/12* (2013.01); *C07C 2102/08* (2013.01)
USPC .......................................... 564/460; 514/657

(58) Field of Classification Search
None
See application file for complete search history.

(56) References Cited

U.S. PATENT DOCUMENTS

| | | | |
|---|---|---|---|
| 3,253,037 A * | 5/1966 | Huebner ...................... 564/428 |
| 5,387,612 A | 2/1995 | Youdim et al. |
| 5,453,446 A | 9/1995 | Youdim et al. |
| 5,457,133 A | 10/1995 | Youdim et al. |
| 5,486,541 A | 1/1996 | Sterling et al. |
| 5,519,061 A | 5/1996 | Youdim et al. |
| 5,532,415 A | 7/1996 | Youdim et al. |
| 5,576,353 A | 11/1996 | Youdim et al. |
| 5,599,991 A | 2/1997 | Youdim et al. |
| 5,668,181 A | 9/1997 | Youdim et al. |
| 5,744,500 A | 4/1998 | Youdim et al. |
| 5,786,390 A | 7/1998 | Youdim et al. |
| 5,891,923 A | 4/1999 | Youdim et al. |
| 6,126,968 A | 10/2000 | Peskin et al. |
| 6,277,886 B1 | 8/2001 | Levy et al. |
| 6,316,504 B1 | 11/2001 | Youdim et al. |
| 6,462,222 B1 | 10/2002 | Chorev et al. |
| 6,630,514 B2 | 10/2003 | Youdim et al. |
| 6,956,060 B2 | 10/2005 | Youdim et al. |
| 7,396,860 B2 | 7/2008 | Blaugrund et al. |
| 7,491,847 B2 | 2/2009 | Frenkel |
| 7,547,806 B2 | 6/2009 | Frenkel et al. |
| 7,572,834 B1 | 8/2009 | Sterling et al. |
| 7,598,420 B1 | 10/2009 | Sterling et al. |
| 7,619,117 B1 | 11/2009 | Lidor-Hadas et al. |
| 7,750,051 B2 | 7/2010 | Frenkel et al. |
| 7,815,942 B2 | 10/2010 | Peskin |
| 7,855,233 B2 | 12/2010 | Frenkel et al. |
| 7,968,749 B2 | 6/2011 | Frenkel et al. |
| 8,080,584 B2 | 12/2011 | Safadi et al. |
| 8,143,315 B2 * | 3/2012 | Stahl ............................. 514/657 |
| 8,334,409 B2 | 12/2012 | Frenkel |
| 8,569,379 B2 | 10/2013 | Petit et al. |
| 8,614,252 B2 | 12/2013 | Frenkel et al. |
| 2003/0065038 A1 * | 4/2003 | Youdim et al. ................. 514/657 |
| 2006/0018957 A1 | 1/2006 | Lerner et al. |
| 2006/0094783 A1 | 5/2006 | Youdim |
| 2007/0100001 A1 | 5/2007 | Youdim et al. |
| 2007/0232700 A1 | 10/2007 | Blaugrund et al. |
| 2009/0062400 A1 | 3/2009 | Oron et al. |
| 2009/0076160 A1 | 3/2009 | Lendvai et al. |
| 2009/0111892 A1 | 4/2009 | Patashnik et al. |
| 2009/0181086 A1 | 7/2009 | Safadi et al. |
| 2009/0312436 A1 | 12/2009 | Levy et al. |
| 2010/0008983 A1 | 1/2010 | Safadi et al. |
| 2010/0137447 A1 | 6/2010 | Lehmann et al. |

(Continued)

FOREIGN PATENT DOCUMENTS

| | | | |
|---|---|---|---|
| WO | 9511016 | * | 4/1995 |
| WO | WO 95/11016 A1 | | 4/1995 |

(Continued)

OTHER PUBLICATIONS

Berge et al., Journal of Phamaceutical Sciences, 66(1), 1977, pp. 1-19.*
U.S. Appl. No. 13/967,240, filed Aug. 14, 2013, Rimkus et al.
U.S. Appl. No. 13/969,295, filed Aug. 16, 2013, Fitzer-Attas et al.
U.S. Appl. No. 14/016,960, filed Sep. 3, 2013, Lehmann et al.
International Search Report, mailed Sep. 3, 2010 in connection with PCT International Application No. PCT/EP2010/059723, filed Jul. 7, 2010.
U.S. Appl. No. 12/283,107, filed Sep. 8, 2008, Sterling et al.
U.S. Appl. No. 13/647,658, filed Oct. 9, 2012, Ulanenko et al.
U.S. Appl. No. 13/647,685, filed Oct. 9, 2012, Safadi et al.
U.S. Appl. No. 13/647,622, filed Oct. 9, 2012, Safadi et al.

(Continued)

*Primary Examiner* — Karl J Puttlitz
(74) *Attorney, Agent, or Firm* — John P. White; Gary J. Gershik; Cooper & Dunham LLP

(57) ABSTRACT

The present invention relates to salts of rasagiline and pharmaceutical preparations thereof. The invention further provides a method of preparing the salts of rasagiline.

14 Claims, No Drawings

(56) References Cited

U.S. PATENT DOCUMENTS

| | | |
|---|---|---|
| 2010/0144887 A1 | 6/2010 | Frenkel et al. |
| 2010/0145101 A1 | 6/2010 | Frenkel et al. |
| 2010/0168239 A1 | 7/2010 | Poewe |
| 2010/0189788 A1 | 7/2010 | Safadi et al. |
| 2010/0189790 A1 | 7/2010 | Safadi et al. |
| 2010/0189791 A1 | 7/2010 | Safadi et al. |
| 2011/0130466 A1 | 6/2011 | Lorenzl |
| 2011/0152381 A1 | 6/2011 | Frenkel et al. |
| 2011/0313050 A1 | 12/2011 | Rimkus et al. |
| 2012/0003310 A1 | 1/2012 | Safadi et al. |
| 2012/0029087 A1 | 2/2012 | Petit et al. |
| 2012/0059058 A1 | 3/2012 | Lorimer et al. |
| 2012/0100189 A1 | 4/2012 | Safadi et al. |
| 2012/0101168 A1 | 4/2012 | Bahar et al. |
| 2012/0238636 A1 | 9/2012 | Patashnik et al. |
| 2012/0263789 A1 | 10/2012 | Safadi et al. |
| 2013/0089610 A1 | 4/2013 | Safadi et al. |
| 2013/0089611 A1 | 4/2013 | Ulanenko et al. |
| 2013/0089612 A1 | 4/2013 | Safadi et al. |

FOREIGN PATENT DOCUMENTS

| | | |
|---|---|---|
| WO | WO 2008/019871 A2 | 2/2008 |
| WO | WO 2008/076315 A1 | 6/2008 |
| WO | WO 2010/070090 | 6/2010 |

OTHER PUBLICATIONS

U.S. Appl. No. 13/651,307, filed Oct. 12, 2012, Levy et al.

International Preliminary Report on Patentability issued Jan. 9, 2012 in connection with PCT International Application No. PCT/EP2010/059723, filed Jul. 7, 2010.

Written Opinion of the International Searching Authority issued Jan. 9, 2012 in connection with PCT International Application No. PCT/EP2010/059723, filed Jul. 7, 2010.

Feb. 17, 2012 Official Action issued by the European Patent Office in connection with European Patent Application No. 10.731734.9.

Aug. 16, 2012 Amendment filed with European Patent Office in connection with European Patent Application No. 10.731734.9.

Sigma-Aldrich, Material Safety Data Sheet "cholest-5-en-3β-yl propionate".

Sigma-Aldrich, Material Safety Data Sheet "ethyl 3-(furan-2-yl)propionate".

Sigma-Aldrich, Material Safety Data Sheet "hydrocortisone 21-caprylate".

Sigma-Aldrich, Material Safety Data Sheet "4-nitrophenyl octanoate".

Sigma-Aldrich, Material Safety Data Sheet "cholesteryl decanoate".

Sigma-Aldrich, Material Safety Data Sheet "phorbol 12-decanoate".

U.S. Appl. No. 13/859,625, filed Apr. 9, 2013, Levy et al.

U.S. Appl. No. 14/092,526, filed Nov. 27, 2013, Levy et al.

U.S. Appl. No. 14/139,212, filed Dec. 23, 2013, Safadi et al.

\* cited by examiner

SALTS OF RASAGILINE AND PHARMACEUTICAL PREPARATIONS THEREOF

CROSS-REFERENCE TO RELATED APPLICATIONS

This application is a §371 national stage of PCT International Application No. PCT/EP2010/059723, filed Jul. 7, 2010, claiming priority of Indian Patent Application No. 1632/CHE/2009, filed Jul. 9, 2009, the contents of each of which in its entirety are hereby incorporated by reference.

The present invention relates to salts of rasagiline and pharmaceutical preparations thereof. The invention further provides a method of preparing the salts of rasagiline.

Rasagiline is the R(+) enantiomer of propargyl-1-aminoindan which is a selective irreversible inhibitor of the B-form of the enzyme monoamine oxidase. Methods for the synthesis of rasagiline are disclosed for example in U.S. Pat. No. 5,532,415 and WO 2002/068376. U.S. Pat. No. 5,532,415 also discloses pharmaceutical compositions which are suitable for the treatment of Parkinson's disease, memory disorder, dementia, depression, hyperactive syndrome, affective illness, neurodegenerative disease, neurotoxic injury, brain ischemia, head trauma injury, spinal trauma injury, schizophrenia, attention deficit disorder, multiple sclerosis, or withdrawal symptoms.

One problem in the preparation of pharmaceutical preparations, in particular solid dosage forms containing rasagiline as active ingredient, is the low content of the active ingredient required in the dosage form. Since the active ingredient has to be admixed with a relatively large amount of excipients, it is difficult to obtain a homogenous distribution of the drug substance in e.g. a tablet blend. If a tablet blend with an insufficient distribution of the drug substance is used in tablet manufacture, the tablets so produced lack content uniformity and do not possess an acceptable drug content. Poor content uniformity has been shown to cause a marked decrease in bioavailability and can also cause toxicity if the amount of drug substance is too high.

To overcome this problem WO 2006/091657 suggests a mixture of particles of a pharmaceutically acceptable salt of rasagiline, wherein more than 90% of the total amount by volume of rasagiline salt particles have a size of less than 250 microns. It is said that the specific particle size distribution has a beneficial effect on the content uniformity of solid pharmaceutical compositions of rasagiline. However, micronization of rasagiline particles has the disadvantage that the powder may be electrostatically charged or may form agglomerates during further processing. Furthermore, micronized drug substances exhibit a decreased flowability which can also result in problems in the further processing steps.

Thus, there is still a need for further forms of the drug substance rasagiline, which are easy to be prepared and which can easily be manufactured into pharmaceutical preparations, in particular solid dosage forms, having a high content uniformity.

Various pharmaceutically acceptable salts of rasagiline are known in the art. For example EP-A-0 436 492 discloses the hydrochloride salt and the tartrate salt of rasagiline. Further salts of rasagiline are disclosed in WO 95/11016, namely the sulphate salt, phosphate salt, mesylate salt, maleate salt, esylate salt, acetate salt, fumarate salt, hydrobromide salt, tosylate salt and benzoate salt. Further salts of rasagiline are disclosed in WO 2008/019871. WO 2008/076315 discloses rasagiline tannate.

However, the known rasagiline salts are either crystalline or amorphous but in any case solid. Thus, all these known salts have the above described problem in the preparation of solid dosage forms.

It has now surprisingly been found that the above problems with regard to content uniformity in pharmaceutical preparations can be overcome by using a liquid salt of rasagiline in the manufacture of the pharmaceutical preparation. Thus, the present invention relates to a salt of rasagiline with an acid, characterized in that the salt is liquid at 23° C.

Liquid salts of rasagiline have the advantage that it is not necessary to micronize the particles before admixing them with excipients in the manufacture of pharmaceutical preparations. Since the salts are liquid they can be easily admixed with large amounts of excipients thereby ensuring a homogenous distribution of the drug substance in the blend and resulting in a high content uniformity in the obtained unit dosage form.

Liquid salts of rasagiline have the further advantage that problems related to crystalline polymorphism do not arise. Solid salts of active pharmaceutical substances that can exist in different crystalline forms often reveal the problem of physical instability when they are stored in pharmaceutical preparations. Since changes of the crystalline form can have tremendous effects on the solubility of a substance, avoidance of the solid state gives a clear benefit.

The salts of the present invention are liquid under normal conditions, i.e. at room temperature (23° C.) and at a normal pressure of 1013 hPa. The term "liquid" means that the salt is in a state of matter where the particles are loose and can freely form a distinct surface at the boundaries of the bulk material. The liquid's shape is determined by the container it fills. The liquid can be of low or high viscosity, e.g. in the form of an oil or thick oil.

In one embodiment of the present invention, the acid which forms part of the liquid salt of rasagiline has the general formula R—COOH, wherein R is a saturated or unsaturated, branched or unbranched $C_2$-$C_{23}$ alkyl. This alkyl residue preferably has 2-19 carbon atoms, more preferably 5-17 carbon atoms. In a further embodiment, those acids are preferred wherein R is a saturated or unsaturated, unbranched $C_2$-$C_{19}$ alkyl, more preferably a $C_5$-$C_{17}$ alkyl.

Examples of suitable acids are propionic acid, butyric acid, pentanoic acid, hexanoic acid, heptanoic acid, octanoic acid, nonanoic acid, decanoic acid, undecanoic acid, lauric acid, tridecanoic acid, myristic acid, pentadecanoic acid, palmitic acid, heptadecanoic acid, stearic acid, nonadecanoic acid, arachidic acid, palmitoleic acid, oleic acid, sorbic acid, linoleic acid, linolenic acid, and arachidonic acid.

It has been found that liquid salts of rasagiline having good physical properties and good chemical stability are obtained using long-chain carboxylic acids like oleic acid and its saturated counter-parts, i.e. acids of high lipophilicity and little hydrogen bonding. Reducing the chain length to 5 carbon atoms still yields liquid products, whereas rasagiline acetate is a crystalline solid. Rasagiline propionate is a solid at 0° C. and an oil at room temperature.

Also stronger but still very lipophilic acids were employed but the resulting salts, such as rasagiline lauryl sulphate and rasagiline dodecyl benzene sulphonate are solids. Even when using docusate, an ion frequently used in the preparation of ionic liquids/liquid salts, the corresponding rasagiline salt is obtained as a solid wax. Also saccharinate, another counterion used in ionic liquid research, results in a rasagiline salt in solid form.

In view of their beneficial properties with respect to synthesis, stability and usefulness in the manufacture of pharmaceutical preparations rasagiline hexanoate, rasagiline octanoate, rasagiline decanoate and rasagiline oleate are the most preferred liquid salts of the present invention.

In a further embodiment, the present invention provides a pharmaceutical preparation comprising a liquid salt of rasagiline as described above. In these pharmaceutical preparations, which are preferably in the form of solid dosage forms, such as capsules, tablets, oral dispersible tablets, sustained release tablets, pellets or granules, preferably tablets, in particular tablets preparable by direct compression, the liquid salt is in admixture with common excipients. For example, the liquid salt can be mixed with the excipients or can be adsorbed on the surface of particulate excipients or can be absorbed into such particles. Thus, the invention allows the preparation of rasagiline formulations of high content uniformity without the need of an undesired micronization step. The liquid salts provide a homogenous distribution of the drug substance in the prepared pharmaceutical preparations. This allows the easy preparation of e.g. 200 mg tablets which contain only 1 mg of rasagiline.

The amount of active ingredient in the pharmaceutical preparation of the present invention is not particularly limited. The amount can be selected by a person skilled in the art on the basis of his general knowledge and the specific requirements. For example, the pharmaceutical preparation can contain 0.2% w/w to 20% w/w active ingredient, calculated as free rasagiline base on the basis of the total weight of the preparation without any optionally present coatings. Preferably, the pharmaceutical composition contains between 5% w/w and 15% w/w active ingredient calculated as free rasagiline base on the basis of the total weight of the preparation without any optionally present coatings.

The pharmaceutical preparations of the present invention may comprise usual pharmaceutically acceptable carriers and/or excipients. For example, if the pharmaceutical preparation is in the form of tablets, these may contain suitable binders, lubricants, disintegrating agents, coloring agents, flavoring agents, flow-enhancing agents, and melting agents. For example, for oral administration in the dosage unit form of a tablet or a capsule, the liquid salt can be combined with an oral, non-toxic, pharmaceutically acceptable, inert carrier, such as lactose, gelantine, agar, starch, succhrose, glucose, methyl cellulose, dicalcium phosphate, calcium sulphate, mannitol, sorbitol, microcrystalline cellulose, and the like. Suitable binders include starch, gelantine, natural sugars such as glucose or beta-lactose, corn starch, natural and synthetic gums such as acacia, tragacanth, or sodium alginate, povidone, carboxymethylcellulose, polyethylene glycol, waxes, and the like. Lubricants used in these dosage forms include sodium oleate, sodium stearate, sodium benzoate, stearic acid, sodium stearyl fumarate, talc, and the like. Disintegrants include, without limitation, starch, methyl cellulose, agar, bentonite, xanthan gum, crosscarmelose sodium, sodium starch glycolate, and the like.

In a preferred embodiment, the pharmaceutical preparation of the present invention is in the form of a tablet, which contains 0.2% w/w to 20% w/w rasagiline calculated as free base, 40% w/w to 98% w/w of one or more fillers, 0% w/w to 40% w/w of one or more binders, 0% w/w to 30% w/w of one or more disintegrants and 0% w/w to 5% w/w of one or more lubricants, each based on the total weight of the preparation without any optionally present coatings.

The pharmaceutical preparations have an excellent content uniformity which can generally not be obtained in particular for directly compressed tablets having a low content of active ingredient of below about 5% w/w.

The present invention also provides a medicament comprising a liquid salt of rasagiline as described above and the use of this liquid salt for the manufacture of such medicament for the treatment of Parkinson's disease, memory disorder, dementia, depression, hyperactive syndrome, affective illness, neurodegenerative disease, neurotoxic injury, brain ischemia, head trauma injury, spinal trauma injury, schizophrenia, attention deficit disorder, multiple sclerosis, or withdrawal symptoms.

The liquid salt of the present invention can be prepared by mixing rasagiline and the acid and recovering the salt. In one embodiment, the mixing step is carried out in the absence of any solvent which has the advantage that it is not necessary to remove any solvent after the salt forming reaction and additionally makes the process environmentally friendly. Yet another advantage of preparing the salt in the absence of a solvent is that the resulting salt does not contain any residual solvents. Efficient mixing can be mediated by the use of a mixer mill. Alternatively, the rasagiline and the acid can be mixed in the presence of a solvent. In this case, either the rasagiline or the acid or the rasagiline and the acid can be suspended or dissolved in the same or different solvents before mixing. For example, first the rasagiline can be dissolved in the solvent and then the acid is added to this solution. Suitable solvents are, e.g., water, tetrahydrofurane, isopropyl alcohol, acetone, diisopropyl ether, and mixtures thereof. Preferred solvents are diisopropyl ether and acetone.

The present invention will now be further illustrated by the following examples, which are not intended to be construed as limiting.

In the following table 1, the reference examples and examples of the present invention are summarized:

TABLE 1

| | Structure | Name | Preparation | Outcome |
|---|---|---|---|---|
| Ref. Ex. 1 | 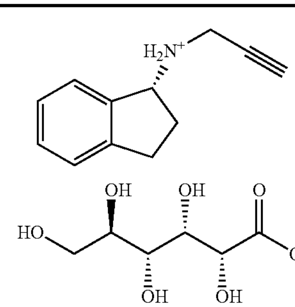 | Gluconate | Prepared from three different solvents | All solid foams |

TABLE 1-continued
| | Structure | Name | Preparation | Outcome |
|---|---|---|---|---|
| Ref. Ex. 2 | 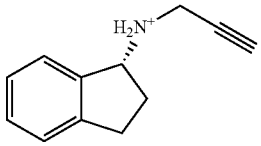 | Aspartate | Prepared in water/IPA | Aspartic acid crystallized |
| Ref. Ex. 3 | 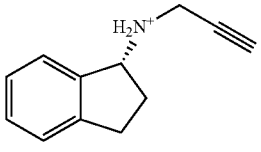 | Citrate | Prepared in warm acetone | Solid foam |
| Ref. Ex. 4 | 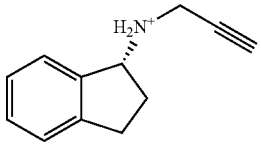 | DL-lactate | Prepared in acetone | Sticky foam |
| Ref. Ex. 5 | 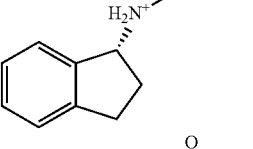 | Saccharinate | Prepared in acetone | Solid foam |
| Ref. Ex. 6 | 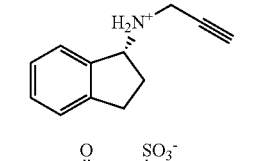 | Docusate | Prepared from the sodium salt as well as from the acid | Solid wax |

TABLE 1-continued

| | Structure | Name | Preparation | Outcome |
|---|---|---|---|---|
| Ref. Ex. 7 | (R)-N-propargyl-1-aminoindan cation with C₁₂H₂₅-O-SO₃⁻ | Lauryl sulphate | Prepared from sodium salt in acetone/water | Solid foam |
| Ref. Ex. 8 | (R)-N-propargyl-1-aminoindan cation with 4-dodecylbenzenesulfonate anion | Dodecyl-benzene-sulphonate | Prepared from sodium salt in acetone/water | Solid foam |
| Ex. 1 | (R)-N-propargyl-1-aminoindan cation with linoleate anion | Linoleate | Prepared in acetone | Yellow oil |
| Ex. 2 | (R)-N-propargyl-1-aminoindan cation with pentanoate anion | Pentanoate | Prepared in diisopropylether | Thick yellow oil |
| Ex. 3 | (R)-N-propargyl-1-aminoindan cation with propanoate anion | Propanoate | Prepared in diisopropylether | Thick yellow oil |
| Ref. Ex. 9 | (R)-N-propargyl-1-aminoindan cation with acetate anion | Acetate | Prepared in diisopropylether | Crystalline solid |

TABLE 1-continued

| | Structure | Name | Preparation | Outcome |
|---|---|---|---|---|
| Ex. 4 | 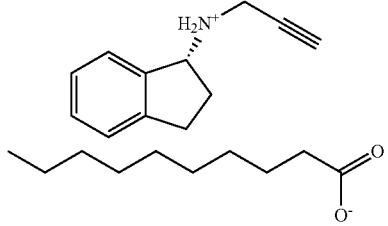 | Decanoate | Prepared in diisopropylether | Yellow oil |
| Ex. 5 | 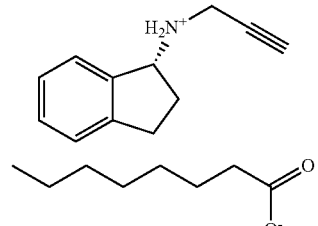 | Octanoate | Prepared in diisopropylether | Yellow oil |
| Ex. 6 | 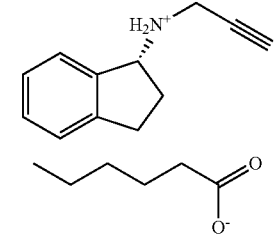 | Hexanoate | Prepared in diisopropylether | Yellow oil |
| Ex. 7 | 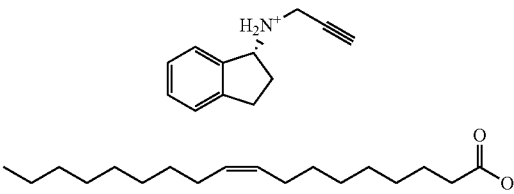 | Oleate | Prepared in diisopropylether | Yellow oil |

REFERENCE EXAMPLE 1

Rasagiline Gluconate a) To a solution of 100 mg (0.58 mmol) rasagiline in 1 ml ethanol 192 µl (0.61 mmol, 1.05 eq) of a 45-50% w/w solution of gluconic acid in water was added. The slightly turbid yellowish solution was stirred for 5H, filtered through cotton wool to remove excess gluconic acid and evaporated. A solid foam was formed.

b) To a solution of 100 mg (0.58 mmol) rasagiline in 1 ml THF 170 µl (0.54 mmol, 0.95 eq) of a 45-50% w/w solution of gluconic acid in water was added. The slightly turbid yellowish solution was stirred for 2 h and an oily layer of less quantity was formed below the THF layer. The supernatant THF was removed and the oily layer washed with THF twice. The residual oily layer became waxy and after drying in high vacuum a solid foam was formed.

c) To a solution of 100 mg (0.58 mmol) rasagiline in 1 ml of a 1:1 mixture of ethanol and water 192 µl (0.61 mmol, 1.05 eq) of a 45-50% w/w solution of gluconic acid in water was added. The clear solution was stirred for 2 h and then evaporated. A solid foam was formed upon drying in high vacuum (211 mg, 0.58 mmol, quant.).

REFERENCE EXAMPLE 2

Rasagiline L-Aspartate 82 mg L-aspartic acid was dissolved in 7 ml water at 70° C. A solution of 100 mg (0.58 mmol) rasagiline in 2 ml isopropanol was added at this temperature. The solution remained clear, was cooled to 0° C. and stirred at this temperature for 1 h. Since no turbidity was observed the solvents were removed in vacuo. The residual clear oil partially crystallised on standing. After a slurry wash with acetone, a white crystalline material was obtained (40 mg). Analysis revealed that this material was aspartic acid.

REFERENCE EXAMPLE 3

Rasagiline Citrate

To a solution of 100 mg (0.58 mmol) rasagiline in 1 ml acetone a solution of 117 mg (0.61 mmol, 1.05 eq) anhydrous citric acid in 1 ml warm acetone was added. The solution became turbid during addition forming a waxy precipitate. The supernatant was removed and the wax was washed with 2 ml acetone twice using sonication. On drying in high vacuum a white solid foam was obtained. Drying was continued for 6 h on high vacuum (120 mg, 0.33 mmol, 57%).

REFERENCE EXAMPLE 4

Rasagiline DL-Lactate

To a solution of 100 mg (0.58 mmol) rasagiline in 1 ml acetone 44 µl (0.58 mmol, 1.0 eq) DL-lactic acid was added. The formation of a white, milky precipitate was observed. After stirring for 2H, a waxy precipitate was formed on the glass wall. The supernatant was removed and the wax was washed with 2 ml acetone. On drying in high vacuum (6 h) a white, sticky solid foam was obtained (150 mg, 0.58 mmol, quant.).

REFERENCE EXAMPLE 5

Rasagiline Saccharinate

To a solution of 100 mg (0.58 mmol) rasagiline in 1.5 ml acetone a solution of 106 mg (0.58 mmol, 1.0 eq) saccharin in 1.5 ml acetone was added. The solution was stirred over night. Evaporation of the solvent in vacuo and drying in high vacuum yielded a white, solid foam (208 mg, 0.58 mmol, quant.).

REFERENCE EXAMPLE 6

Rasagiline Docusate a) 260 mg (0.58 mmol) sodium docusate was dissolved in 1 ml acetone. 40 µl acetic acid was added. The resulting solution was added to a solution of 100 mg (0.58 mmol) rasagiline in 1 ml acetone. After stirring over night, 2 ml dichloromethane was added and the mixture was filtered through cotton wool. The filtrate was evaporated to yield a solid waxy material.
b) Sodium docusate was converted into the corresponding acid by aqueous work-up with 1 M hydrochloric acid and dichloromethane. The organic phase was dried and evaporated. 245 mg (0.58 mmol) of the resulting acid was dissolved in 1 ml acetone and added to a solution of 100 mg (0.58 mmol) rasagiline in 1 ml acetone. After stirring for 2 h the solvent was evaporated to yield a solid waxy material (365 mg, 0.58 mmol, quant.).

REFERENCE EXAMPLE 7

Rasagiline Lauryl Sulphate 167 mg (0.58 mmol, 1.0 eq) sodium lauryl sulphate was dissolved in 1 ml water and 40 µl acetic acid followed by addition of a solution of 100 mg (0.58 mmol) rasagiline in 1 ml acetone. After stirring for 2 h the solution was evaporated in vacuo. The residue was reslurried in 2 ml acetone and 1 ml methanol. The mixture was filtered through cotton wool to remove sodium acetate. The filtrate was evaporated to yield a solid foam.

REFERENCE EXAMPLE 8

Rasagiline 4-dodecylbenzenesulfonate 202 mg (0.58 mmol, 1.0 eq) sodium 4-dodecylbenzenesulfonate was dissolved in 1 ml water and 40 µl acetic acid was added. The resulting solution was added to a solution of 100 mg (0.58 mmol) rasagiline in 1 ml acetone. After stirring for 2H, the solution was evaporated in vacuo. The residue was reslurried in 2 ml acetone. The mixture was filtered through cotton wool to remove sodium acetate. The filtrate was evaporated to yield a solid foam (300 mg, 0.58 mmol, quant.).

EXAMPLE 1

Rasagiline Linoleate

To a solution of 300 mg rasagiline (1.75 mmol) in 6 ml acetone 0.54 ml (1.75 mmol, 1.0 eq) linoleic acid was added. After stirring for 2 h the solvent was evaporated at 30° C. in vacuo. Drying in high vacuum led to a brownish oil (0.77 g, 1.75 mmol, quant.).

IR: ν=3308.9, 3009.2, 2927.2, 2854.8, 1712.2, 1615.9, 1548.5, 1459.5, 753.8 $cm^{-1}$. IR indicates protonation of the amine.

EXAMPLE 2

Rasagiline Pentanoate

To a solution of 60 mg (0.58 mmol, 1.0 eq) pentanoic acid in 0.5 ml diisopropyl ether a solution of 100 mg (0.58 mmol) rasagiline in 0.5 ml diisopropyl ether was added. After stirring for 90 min the solvent was removed in vacuo. The residue was dried in high vacuum for 5 h to yield a thick oil (158 mg, 0.58 mmol, quant.).

$^1$H NMR ($d_6$-DMSO, 400 MHz): δ=7.30 (m, 1 H, PhH), 7.23-7.12 (m, 3 H, PhH), 4.24 (t, J=6.4 Hz, 1 H, N—CH), 3.37 (d, J=2.4 Hz, 2 H, N—$CH_2$), 3.09 (t, J=2.4 Hz, 1 H, alkynyl-H), 2.89 (m, 1 H, ring-CH), 2.72 (quint., J=15.0, 7.6 Hz, 1 H, ring-CH), 2.27 (m, 1 H, ring-CH), 2.19 (t, J=7.4 Hz, 2 H, C(O)$CH_2$), 1.74 (m, 1 H, ring-CH), 1.47 (m, 2 H, C(O)$CH_2CH_2$), 1.29 (m, 2 H, $CH_3CH_2$), 0.86 (t, J=7.6 Hz, 3 H, $CH_3$). The integrals confirm a ratio of amine/acid=1:1.

IR: ν=3291.5, 2957.6, 2932.9, 1712.3, 1606.7, 1552.1, 1458.4, 754.9, 661.6 $cm^{-1}$. IR indicates protonation of the amine.

EXAMPLE 3

Rasagiline Propanoate

To a solution of 43 mg (0.58 mmol, 1.0 eq) propionic acid in 0.5 ml diisopropyl ether a solution of 100 mg (0.58 mmol) rasagiline in 0.5 ml diisopropyl ether was added. After stirring for 90 min the solvent was removed in vacuo. The residue was dried in high vacuum for 5 h to yield a thick oil (143 mg, 0.58 mmol, quant.).

$^1$H NMR ($d_6$-DMSO, 400 MHz): δ=7.30 (m, 1 H, PhH), 7.24-7.10 (m, 3 H, PhH), 4.25 (t, J=6.4 Hz, 1 H, N—CH), 3.38 (dd, J=2.4, 1.2 Hz, 2 H, N—$CH_2$), 3.09 (t, J=2.4 Hz, 1 H, alkynyl-H), 2.90 (m, 1 H, ring-CH), 2.72 (quint., J=15.0, 7.6 Hz, 1 H, ring-CH), 2.28 (m, 1H, ring-CH), 2.19 (q, J=7.6 Hz, 2 H, C(O)$CH_2$), 1.74 (m, 1 H, ring-CH), 0.99 (t, J=7.6 Hz, 3 H, $CH_3$). The integrals confirm a ratio of amine/acid=1:1.

IR: ν=3291.7, 2930.4, 2852.3, 1716.1, 1599.2, 1560.0, 1459.1, 754.7, 648.3 $cm^{-1}$. IR indicates protonation of the amine.

REFERENCE EXAMPLE 9

Rasagiline Acetate

To a solution of 100 mg (0.58 mmol) rasagiline in 1.5 ml diisopropyl ether 33 µl acetic acid was added. After stirring for 1H, the solvent was removed in vacuo during which precipitation was observed. After drying in high vacuum for 2 h a crystalline solid was obtained.

EXAMPLE 4

Rasagiline Decanoate

To a solution of 6.0 g (35.0 mmol) rasagiline in 120 ml diisopropyl ether 6.75 ml (35.0 mmol, 1.0 eq) decanoic acid was added under nitrogen. After stirring for 90 min, the solvent was removed in vacuo at 30° C. Drying on the rotary evaporator continued for another 2 h at this temperature. Drying in high vacuum for 2 h yielded 11.5 g (33.5 mmol, 96%) of a yellow oil.

$^1$H NMR (d$_6$-DMSO, 300 MHz): δ=7.32 (m, 1 H, PhH), 7.21-7.12 (m, 3 H, PhH), 4.25 (t, J=6.3 Hz, 1 H, N—CH), 3.37 (d, J=2.4 Hz, 2 H, N—CH$_2$), 3.05 (t, J=2.4 Hz, 1 H, alkynyl-H), 2.91 (m, 1 H, ring-CH), 2.74 (quint., J=15.0, 7.5 Hz, 1 H, ring-CH), 2.28 (m, 1 H, ring-CH), 2.17 (t, J=7.5 Hz, 2 H, C(O)CH$_2$), 1.76 (m, 1 H, ring-CH), 1.47 (brt, J=6.9 Hz, 2 H, C(O)CH$_2$CH$_2$), 1.23 (s, 12 H, 6×CH$_2$), 0.85 (t, J=6.3 Hz, 3 H, ω-CH$_3$). The integrals confirm a ratio of amine/acid=1:1.

IR: ν=2925.62, 2854.60, 1713.00, 1616.02, 1548.12, 1459.44, 1401.58 cm$^{-1}$. IR indicates protonation of the amine.

HPLC (by area %): 99.81%.

EXAMPLE 5

Rasagiline Octanoate a) To a solution of 6.0 g (35.0 mmol) rasagiline in 120 ml diisopropyl ether 5.5 ml (35.0 mmol, 1.0 eq) octanoic acid was added under nitrogen. After stirring for 90 min, the solvent was removed in vacuo at 30° C. Drying on the rotary evaporator was continued for another 2 h at this temperature. Drying in high vacuum for 2 h yielded 10.9 g (34.6 mmol, 99%) of a light brown oil.

$^1$H NMR (d$_6$-DMSO, 300 MHz): δ=7.31 (m, 1 H, PhH), 7.21-7.13 (m, 3 H, PhH), 4.25 (t, J=6.3 Hz, 1 H, N—CH), 3.37 (d, J=2.8 Hz, 2 H, N—CH$_2$), 3.05 (t, J=2.4 Hz, 1H, alkynyl-H), 2.91 (m, 1 H, ring-CH), 2.74 (quint., J=15.0, 7.5 Hz, 1 H, ring-CH), 2.28 (m, 1 H, ring-CH), 2.17 (t, J=7.5 Hz, 2 H, C(O)CH$_2$), 1.76 (m, 1 H, ring-CH), 1.48 (brt, J=6.9 Hz, 2 H, C(O)CH$_2$CH$_2$), 1.24 (s, 8 H, 4×CH$_2$), 0.85 (t, J=6.3 Hz, 3 H, ω-CH$_3$). The integrals confirm a ratio of amine/acid=1:1.

IR: ν=2954.71, 2927.69, 2855.59, 1713.63, 1607.76, 1548.75, 1459.54, 1401.97 cm$^{-1}$. IR indicates protonation of the amine.

HPLC (by area %): 99.58%.

b) 1.0 g (5.84 mmol) rasagiline and 0.93 ml (5.84 mmol, 1.0 eq) octanoic acid were milled in a 5 ml agate jar with a 10 mm agate ball at 20 Hz in a Retsch MM400 ball mill for 30 min. Rasagiline octanoate was obtained as a yellow viscous oil. The IR spectroscopic data was in agreement with the data obtained in example 5 a).

EXAMPLE 6

Rasagiline Hexanoate

To a solution of 7.0 g (40.9 mmol) rasagiline in 120 ml diisopropyl ether 5.1 ml (40.9 mmol, 1.0 eq) hexanoic acid was added under nitrogen. After stirring for 90 min, the solvent was removed in vacuo at 30° C. Drying on the rotary evaporator was continued for another 2 h at this temperature. Drying in high vacuum for 2 h yielded 11.6 g (40.3 mmol, 99%) of a light brown oil.

$^1$H NMR (d$_6$-DMSO, 300 MHz): δ=7.31 (m, 1 H, PhH), 7.21-7.10 (m, 3H, PhH), 4.25 (t, J=6.3 Hz, 1 H, N—CH), 3.37 (d, J=2.8 Hz, 2 H, N—CH$_2$), 3.06 (t, J=2.4 Hz, 1 H, alkynyl-H), 2.90 (m, 1 H, ring-CH), 2.74 (quint., J=15.0, 7.5 Hz, 1 H, ring-CH), 2.28 (m, 1 H, ring-CH), 2.17 (t, J=7.5 Hz, 2 H, C(O)CH$_2$), 1.74 (m, 1 H, ring-CH), 1.48 (quint., J=14.4, 7.2 Hz, 2 H, C(O)CH$_2$CH$_2$), 1.25-1.21 (m, 4 H, 2×CH$_2$), 0.85 (t, J=6.6 Hz, 3 H, ω-CH$_3$). The integrals confirm a ratio of amine/acid=1:1.

IR: ν=2956.13, 2931.46, 2859.22, 1714.75, 1608.88, 1551.24, 1459.09, 1401.15 cm$^{-1}$. IR indicates protonation of the amine.

HPLC (by area %): 99.63%.

EXAMPLE 7

Rasagiline Oleate a) To a solution of 4.5 g (26.3 mmol) rasagiline in 120 ml diisopropyl ether 8.3 ml (26.3 mmol, 1.0 eq) oleic acid was added under nitrogen. After stirring for 90 min, the solvent was removed in vacuo at 30° C. Drying on the rotary evaporator was continued for another 2 h at this temperature. Drying in high vacuum for 2 h yielded 11.2 g (24.7 mmol, 94%) of a yellow oil.

$^1$H NMR (d$_6$-DMSO, 300 MHz): δ=7.31 (m, 1 H, PhH), 7.21-7.10 (m, 3 H, PhH), 5.30 (t, J=4.8 Hz, 2 H, olefin-H), 4.25 (t, J=6.3 Hz, 1 H, N—CH), 3.37 (d, J=2.8 Hz, 2 H, N—CH$_2$), 3.04 (t, J=2.4 Hz, 1 H, alkynyl-H), 2.90 (m, 1 H, ring-CH), 2.71 (quint., J=15.0, 7.5 Hz, 1 H, ring-CH), 2.26 (m, 1 H, ring-CH), 2.15 (t, J=7.5 Hz, 2 H, C(O)CH$_2$), 1.97 (m, 4 H, 2×C=CHCH$_2$), 1.76 (m, 1 H, ring-CH), 1.48 (brt, J=7.2 Hz, 2 H, C(O)CH$_2$CH$_2$), 1.25-1.21 (s, 18 H, 9×CH$_2$), 0.84 (t, J=6.3 Hz, 3 H, ω-CH$_3$). The integrals show a ratio of amine/acid=1:1.

IR: ν=2925.56, 2854.04, 1712.92, 1615.04, 1551.28, 1459.31, 1402.52 cm$^{-1}$. IR indicates protonation of the amine.

HPLC (by area %): 99.80%.

b) 20 mg (0.12 mmol) rasagiline was added to 33 mg (0.12 mmol, 1.0 eq) oleic acid in a glass vial. The mixture was shaken by hand for 5 min to form a homogenous oil and let stand at room temperature for 1 h. The IR spectroscopic data was in agreement with the data obtained in example 7 a).

EXAMPLE 8

Preparation of Tablets

Tablets consisting of 1 mg rasagiline (calculated as free base), 175 mg silicified microcrystalline cellulose (Prosolv®), 25 mg croscarmellose sodium (Ac-Di-Sol®), and 0.83 mg magnesium stearat were prepared as follows: A premix of 2 g Prosolv® and the oily rasagiline salt was prepared in a mortar. The remaining amount of Prosolv®, Ac-Di-Sol®, and magnesium stearat was added and mixid intensively. Tablets were prepared in a Riva Minipress with a compression force of 3.5 kN. They showed excellent content uniformity.

The invention claimed is:

1. A rasagiline salt with an acid, wherein the salt is a liquid at 23° C., and wherein the acid part of the salt is selected from the group consisting of pentanoic acid, hexanoic acid, heptanoic acid, nonanoic acid, lauric acid, tridecanoic acid, myristic acid, pentadecanoic acid, palmitic acid, heptadecanoic acid, nonadecanoic acid, arachidic acid, palmitoleic acid, oleic acid, linoleic acid, linolenic acid, and arachidonic acid.

2. The salt according to claim 1, selected from the group consisting of rasagiline hexanoate and rasagiline oleate.

3. A pharmaceutical preparation comprising the rasagiline salt according to claim 1.

4. A method of treating a subject afflicted with Parkinson's disease, memory disorder, dementia, depression, hyperactive syndrome, affective illness, neurodegenerative disease, neurotoxic injury, brain ischemia, head trauma injury, spinal trauma injury, schizophrenia, attention deficit disorder, multiple sclerosis, or withdrawal symptoms comprising administering to the subject the rasagiline salt of claim 1.

5. A method of preparing the rasagiline salt according to claim 1, comprising:
   a) mixing rasagiline and the acid, and
   b) recovering the salt.

6. The method according to claim 5, wherein the rasagiline and the acid are mixed by using a mixer mill.

7. The method according to claim 5, wherein the rasagiline and the acid are mixed in the presence of a solvent.

8. The method according to claim 7, wherein the solvent is diisopropyl ether or acetone.

9. A pharmaceutical preparation comprising the rasagiline salt according to claim 2.

10. A method of treating a subject afflicted with Parkinson's disease, memory disorder, dementia, depression, hyperactive syndrome, affective illness, neurodegenerative disease, neurotoxic injury, brain ischemia, head trauma injury, spinal trauma injury, schizophrenia, attention deficit disorder, multiple sclerosis, or withdrawal symptoms comprising administering to the subject the rasagiline salt of claim 2.

11. A method of preparing the rasagiline salt according to claim 2, comprising:
   a) mixing rasagiline and the acid, and
   b) recovering the salt.

12. The method according to claim 11, wherein the rasagiline and the acid are mixed by using a mixer mill.

13. The method according to claim 11, wherein the rasagiline and the acid are mixed in the presence of a solvent.

14. The method according to claim 13, wherein the solvent is diisopropyl ether or acetone.

* * * * *